United States Patent [19]
Rosengart

[11] Patent Number: 5,868,764
[45] Date of Patent: Feb. 9, 1999

[54] PERFUSION AND OCCLUSION DEVICE AND METHOD

[75] Inventor: Todd K. Rosengart, Tenafly, N.J.

[73] Assignee: Cornell Research Foundation, Inc., Ithaca, N.Y.

[21] Appl. No.: 764,447

[22] Filed: Dec. 12, 1996

[51] Int. Cl.[6] .................................................. A61B 17/04
[52] U.S. Cl. ........................ 606/153; 606/155; 128/842
[58] Field of Search .................................. 606/152–156; 128/831, 842

[56] References Cited

U.S. PATENT DOCUMENTS

| | | |
|---|---|---|
| 3,435,824 | 4/1969 | Gamponia . |
| 3,826,241 | 7/1974 | Bucalo . |
| 3,831,584 | 8/1974 | Bucalo . |
| 3,951,132 | 4/1976 | Bucalo . |
| 3,991,767 | 11/1976 | Miller . |
| 4,168,708 | 9/1979 | Lepley . |
| 4,230,119 | 10/1980 | Blum . |
| 4,674,506 | 6/1987 | Alcond . |
| 4,721,109 | 1/1988 | Healey . |
| 4,753,236 | 6/1988 | Healey . |
| 4,932,421 | 6/1990 | Kaali et al. .............................. 128/831 |
| 4,946,463 | 8/1990 | Wright . |
| 5,036,868 | 8/1991 | Berggren . |
| 5,037,428 | 8/1991 | Picha . |
| 5,192,289 | 3/1993 | Jessen . |
| 5,323,789 | 6/1994 | Berggren . |
| 5,425,739 | 6/1995 | Jessen . |

*Primary Examiner*—Gary Jackson
*Attorney, Agent, or Firm*—Jones, Tuller & Cooper, P.C.

[57] ABSTRACT

The present invention on embodies a device and method for creating a bloodless field at an incision site in a blood vessel. The invention includes a perfusion tube for allowing perfusion of blood past the incision site. A pair of conical occlusive members are mounted on either end of the perfusion tube for preventing blood from flowing into the surgical site. A tubular stem depends from the tube, and includes a movable stopper which may be moved between a first position for blocking blood flow through the perfusion tube, and a second position for enabling blood to perfuse through the perfusion tube. With the movable stopper in the first position, a first end of the device may be inserted through a small incision into the upstream side of a blood vessel so that the blood flow is blocked. The second end of the device may then be inserted in the downstream side of the incision. The stopper may then be moved to the second position so that blood is free to flow through the perfusion tube. The downstream tissue will thus continue to receive a supply of oxygenated blood, while the portion of the blood vessel between the occlusive members remains blood-free.

17 Claims, 2 Drawing Sheets

PERFUSION AND OCCLUSION DEVICE AND METHOD

FIELD OF THE INVENTION

This invention is directed to a surgical medical instrument. Specifically, the device is suitable for use in creating a bloodless field in a portion of a blood vessel during surgery, while allowing blood to perfuse past the surgical field. One particular application to which this invention may be applied is the creation of a bloodless anastomosis site in a blood vessel during a coronary artery by-pass operation.

DESCRIPTION OF THE PRIOR ART

In surgical procedures, it is often necessary to seal-off a portion of a tubular organ, such as a blood vessel. This need often may arise in vascular surgery, and, in particular, in a coronary artery by-pass operation, which is a procedure whereby blood is routed around a blocked portion of a coronary artery to restore adequate blood supply to the heart muscle downstream of the artery blockage. In a by-pass operation, a short segment of tubular graft material, either artificial tubing or a vein taken from a donor site on the patient, is connected between the patient's aorta and the blocked coronary artery at a point below the blockage. This by-pass is known as an "anastomosis", and enables oxygenated blood to by-pass the blockage in the artery by flowing through the tubular graft to enter the artery at a location downstream of the blockage.

One conventional operating technique for a coronary artery bypass requires clamping-off the aorta to terminate blood flow to all of the coronary arteries. Surgical connection of the tubular grafts then proceeds by creating incisions (arteriotomies) in the arteries, and suturing the ends of the tubular grafts over the incisions in a substantially blood-tight fashion. To prevent blood from flowing out of the arteriotomies during the surgical procedure, it is necessary to clamp-off the aorta or the individual arteries. This can deny blood flow to the muscle tissue of the heart for an extended period of time, particularly where multiple by-passes are being performed. The prolonged restriction of blood supply to the heart tissue can result in further damage to already oxygen-starved tissue.

One device which is designed to address this problem is disclosed in U.S. Pat. No. 4,230,119, to Lepley et al., which describes an occlusive device for placement in the coronary artery during anastomosis procedures. The device includes a bar with a pair of conical occlusive bulbs on either end. A handle depends from the bar to enable placement of the device within an artery. The device is inserted into an artery at the anastomosis site. The occlusive bulbs are sized so as to block blood flow through the artery at the anastomosis site. The occlusive device is removed from the artery just prior to placement of the final stitches joining the tubular graft to the artery. However, while the Lepley device is an improvement over the previous technique of clamping the aorta, it still denies blood flow to the tissue downstream of the anastomosis site.

A device similar to Lepley's is disclosed in U.S. Pat. No. 4,230,119, to Blum, which describes a micro-hemostat which allows perfusion of blood through the anastomosis site while the artery is occluded. The Blum device includes a tube having a pair of inflatable cuffs located at either end. The Blum device is inserted into an artery in a fashion similar to the Lepley device, and the cuffs are inflated to block the artery at the anastomosis site. Blood is able to continue to flow downstream of the anastomosis site by passing through the tube. However, the necessity of having inflatable cuffs and an inflation means increases the cost and the complexity of the Blum device. In addition, when the Blum device is being inserted, blood is free to flow out of the tube, which can obstruct the surgeon's view of the surgical field.

Consequently, from an examination of the prior art, it is apparent that a need exists for an improved method and apparatus for creating a bloodless field at an anastomosis site. The present invention overcomes the shortcomings associated with the above-described devices, and provides a substantial advancement in the art.

SUMMARY OF THE INVENTION

The present invention embodies a novel occlusion device and method for creating a bloodless field at an incision site in a blood vessel. The invention includes a perfusion tube for allowing perfusion of blood past the incision site. A pair of bulbous conical occlusive members are mounted on either end of the tube for preventing blood from flowing into the surgical site. A tubular stem depends from the tube, and includes a movable stopper which acts as a valve, and which may be moved between a first position for blocking blood flow through the perfusion tube, and a second position for enabling blood to perfuse through the perfusion tube.

With the movable stopper in the first position, a first end of the device may be inserted through a small incision in a blood vessel so that the upstream blood flow is blocked. The second end of the device may then be inserted in the downstream side of the incision. After the device has been inserted, the stopper may be moved to the second position so that blood is free to flow through the perfusion tube. The downstream tissue will thus continue to receive a supply of oxygenated blood, while the portion of the blood vessel between the occlusive members remains blood-free.

The showings of the Figures are enlarged to facilitate the disclosure of the invention.

DESCRIPTION OF THE PREFERRED EMBODIMENT

Figure 1:
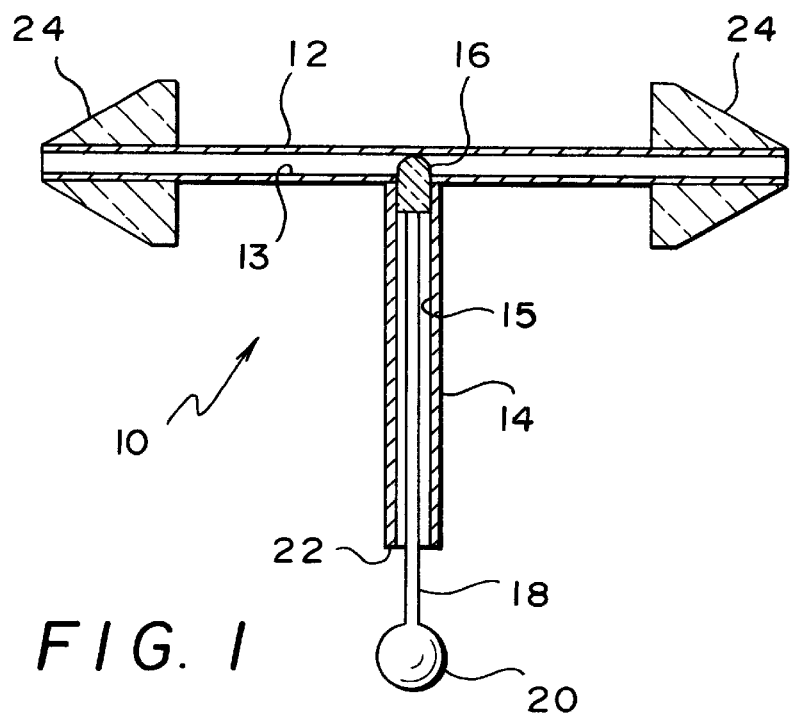
FIG. 1 is a side elevation in cross section of the occlusion device of the present invention.

The invention is directed to a device which enables the occlusion of a portion of a tubular organ, such as a blood vessel, for creating a bloodless surgical field, while simultaneously allowing blood to be perfused to an area downstream of the surgical field. FIG. 1 illustrates a preferred embodiment of the occlusion device 10 of the present invention. Occlusion device 10 includes a perfusion tube 12 having a lumen 13. Perfusion tube 12 is formed from flexible tubing of polyethylene, polyurethane, or any other suitable bio-compatible material, and is preferably coated with heparin or a similar anticoagulant to prevent the formation of blood clots during use. The heparin coating may be over the entire surface of perfusion tube 12, but is at least on the surface of lumen 13.

A tubular stem 14 has a lumen 15 of the same or slightly greater inner diameter as lumen 13 of perfusion tube 12. Tubular stem 14 is attached approximately at the mid-point of perfusion tube 12, and depends generally obliquely from perfusion tube 12. Tubular stem 14 may be made of a the same material as perfusion tube 12, but is preferably of a slightly stiffer material to facilitate manipulation and handling of occlusion device 10. Tubular stem 14 may be attached to perfusion tube 12 by adhesive, ultrasonic welding, or any other suitable means.

A valve arrangement is associated with lumen 13 of perfusion tube 12 for controlling the flow of fluid therethrough. Lumen 15 of tubular stem 14 is in communication with lumen 13 of perfusion tube 12 so that a stopper 16, which acts as a valve, may be slid through the lumen 15 of tubular stem 14 and into lumen 13 of perfusion tube 12. In this manner lumen 13 of perfusion tube 12 is occluded by stopper 16 when the stopper is disposed within lumen 13 of perfusion tube 12. When stopper 16 is partially withdrawn into lumen 15 of tubular stem 14, fluid is free to pass through lumen 13 of perfusion tube 12.

Stopper 16 may be constructed from silicone rubber, butyl rubber, or similar resilient materials, and is mounted on a stopper handle 18 which may be a piece of stainless steel wire or other stiff material. A grip tab 20 may be included on the end of stopper handle 18 to enable the stopper handle to be gripped more easily. In addition, stopper handle 18 may be colored or otherwise marked in the area disposed near the free end 22 of tubular stem 14 so that a surgeon may quickly determine whether stopper 16 is disposed in lumen 13 of perfusion tube 12.

Furthermore, while stopper 16 is movable in a reciprocating manner, in and out of lumen 13 of perfusion tube 12, for controlling the blood flow therethrough, it will be apparent that the blood flow may be controlled by other valve arrangements. For example, stopper 16 may have hole through it, and stopper handle 18 may be rotated to rotate stopper 16 from a position in which blood may flow through the hole in stopper 16, to a position in which blood may not flow through. Other similar valve designs may also be used in place of stopper 16.

A bulbous occlusive member 24 is located on each end of perfusion tube 12 in an annular manner so that blood is free to enter lumen 13 of perfusion tube 12 when perfusion tube 12 is disposed within a blood vessel. Occlusive members 24 may be constructed from silicone rubber, butyl rubber, or other soft, smooth, resilient bio-compatible materials. It is preferred that occlusive members 24 be sufficiently soft to avoid injury to the interior of the blood vessel, while also being of sufficient hardness to be capable of forming a good seal with the interior wall of the blood vessel. A Shore A durometer in the range of 25 to 60, is suitable for most applications. In addition, while occlusive members 24 are shown as truncated cones in the drawings, it will be readily apparent to those skilled in the art that occlusive members 24 could be spherical, bullet-shaped, or otherwise shaped so as to form an occlusive configuration. In addition, the occlusive members may be in the shape of hollow cones so that the outer edges of the cones will flex inward when forming a seal with the interior of a vessel.

Occlusive members 24 may be formed by molding them directly onto perfusion tube 12, or they may be formed separately and then attached to perfusion tube 12 using adhesive or similar means. In addition, occlusive members 24 may be coated with a hydrophilic polymer such as ethylene oxide, polyethylene glycol acrylate, or similar lubricous material which will facilitate insertion of occlusive members 24 into a vessel lumen.

Occlusive members 24 are dimensioned in accordance with the size of the blood vessel which they are intended to occlude. A series of occlusion devices 10 having occlusive members 24 of different diameters may be provided. For use in coronary arteries it may be desirable to provide a series of devices ranging in diameter from 1 millimeter to 3 millimeters in 0.5 millimeter increments. The length of perfusion tube 12 from tip to tip typically ranges from about 15 to 25 millimeters. The length of tubular stem 14, while not as critical as the other dimensions, typically would be approximately 30 to 60 millimeters, with stopper handle 18 extending approximately another 10 to 30 millimeters beyond, the free end 22 of tubular stem 14 when stopper 16 is disposed in lumen 13 of perfusion tube 12.

Perfusion tube 12 must be sufficiently flexible to flex during insertion and removal, while also being stiff enough to not to buckle axially when being inserted or when in place in a vessel. The stiffness and buckling properties of perfusion tube 12 may be controlled by controlling the material, the wall thickness, and the diameter of the tube used. In addition, the diameter of perfusion tube 12 is somewhat dependent upon the vessel diameter with which occlusion device 10 is intended to be used. For example, if occlusive members 24 have an outer diameter of 1 millimeter, the outer diameter of perfusion tube 12 would preferably be approximately 0.5 millimeters. However, if the outer diameter of occlusive members 24 is 3 millimeters, then the outer diameter of perfusion tube 12 may be approximately 1.5 millimeters.

Figure 2:
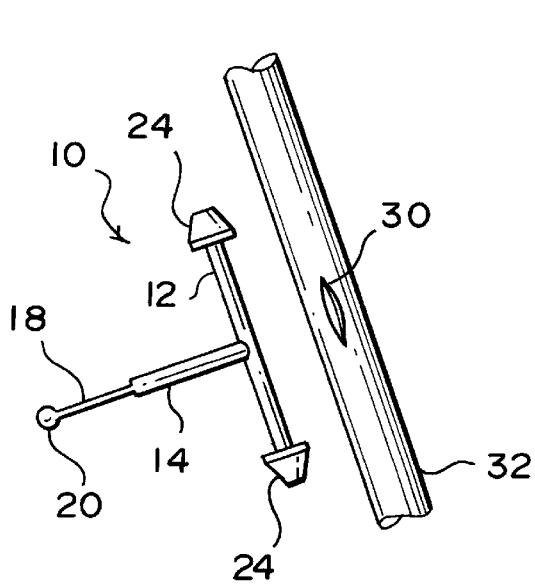
FIG. 2 shows the device of FIG. 1 during use in a surgical procedure prior to insertion.
Figure 3:
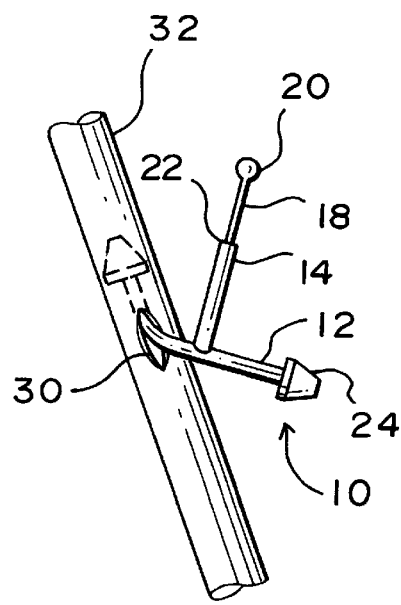
FIG. 3 show the device of FIG. 1 during use in a surgical procedure partially inserted.
Figure 4:
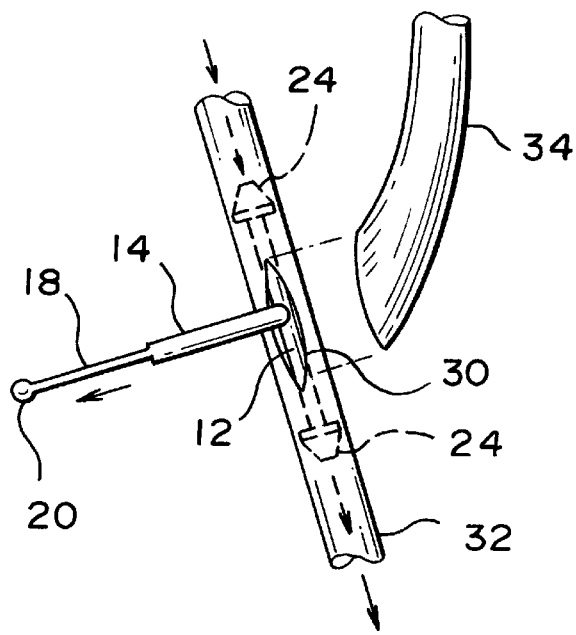
FIG. 4 shows the device of FIG. 1 during use in a surgical procedure fully inserted.
Figure 5:
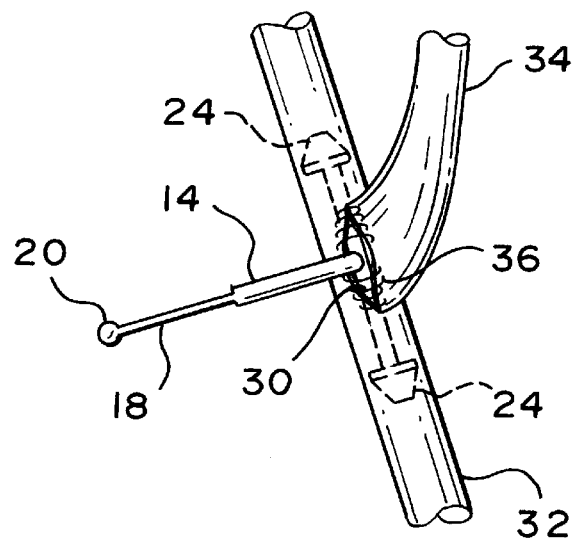
FIG. 5 shows the device of FIG. 1 during use in a surgical procedure prior to removal.

In use, referring to FIGS. 2–5, a small longitudinal incision 30 is initially made in the portion of a blood vessel 32 to be anastomotized, as illustrated in FIG. 2. A first end of perfusion tube 12 is inserted into the upstream or antegrade side of incision 30 so that an occlusive member 24 blocks the blood flow, as illustrated in FIG. 3. The diameter of occlusive member 24 to be used is chosen so as to be slightly larger than the inner diameter of blood vessel 32. The insertion of first occlusive member 24 stops the blood flow through vessel 32, and since stopper 16 is in place in lumen 13 of perfusion tube 12, there is no blood flow through perfusion tube 12 either. Incision 30 may then be extended to the desired length for creating the anastomosis. The second end of perfusion tube 12 is then inserted into the downstream side of vessel 32. Stopper 16 is then withdrawn from lumen 13 of perfusion tube 12 by pulling stopper handle 18 outwardly while holding tubular stem 14 immobile. The withdrawal of stopper 16 into lumen 15 of tubular stem 14 allows blood to perfuse through perfusion tube 12 to the downstream side of vessel 32, while the anastomosis site remains blood free.

A tubular graft 34 may then be sutured to blood vessel 32 at incision 30. A plurality of sutures 36 are formed about the opening through which tubular stem 14 extends, but sutures 36 are not drawn tight. When sutures 36 are formed, but before they are drawn tight, stopper 16 is pushed back down to occlude the lumen of perfusion tube 12. The downstream end of perfusion tube 12 is then withdrawn from vessel 32 through the opening in the sutures 36. The upstream end of perfusion tube 12 is then withdrawn, and the sutures quickly drawn tight to minimize blood loss. Additional sutures are added as required to prevent leakage at the graft/vessel interface.

Although preferred embodiments have been described herein, it will be recognized that a variety of changes and modifications may be made without departing from the spirit of the subject invention, the scope of which is set forth in the following claims.

What is claimed is:

1. A device removably insertable through an incision in a blood vessel for creating a bloodless field during a blood vessel anastomosis procedure, said device comprising:

a tubular member having a lumen for allowing the passage of blood therethrough, said tubular member being sufficiently flexible to facilitate insertion and removal of said device through an incision by flexing of said tubular member;

occlusive members located at either end of said tubular member, said occlusive members having a diameter which enables said occlusive members to be inserted through the incision and into the lumen of the blood vessel for stopping the flow of blood out of said blood vessel; and a valve for controlling blood flow through said tubular member, said valve being movable from a first position in which flow through said lumen of said tubular member is blocked, to a second position in which said lumen of said tubular member is open so that blood may pass through said lumen.

2. The device of claim 1, wherein said occlusive members are shaped as truncated cones.

3. The device of claim 1, in which a stem is attached to said tubular member to facilitate removal of said device from the incision.

4. The device of claim 1, wherein a tubular stem is attached to said tubular member, and wherein said valve includes a stopper mounted on a stopper handle, said stopper and said stopper handle being movable within said tubular stem by moving said stopper handle in a reciprocating manner relative to said tubular stem, whereby said stopper may be moved between a first position in which flow through said lumen is blocked, and a second position in which said lumen is open.

5. The device of claim 4, in which said stopper handle includes a tab for gripping said stopper handle.

6. A device removably insertable into an incision in a blood vessel for permitting perfusion of blood past an anastomosis site during anastomosis of a bypass to a blood vessel, said device comprising:

a perfusion tube having a lumen for enabling blood to pass through said lumen from one side of the anastomosis site to another, said perfusion tube being of a flexible material;

a bulbous occlusive member located at either end of said perfusion tube, said bulbous occlusive members being of sufficient size for forming a sealing engagement with the inner wall of the blood vessel, while also being shaped to be removable from said sealing engagement; and a valve disposed in said lumen for controlling the flow of blood through said perfusion tube.

7. The device of claim 6, further including a tubular stem connected approximately to the midpoint of said perfusion tube.

8. The device of claim 6, wherein said bulbous occlusive members are shaped as truncated cones.

9. The device of claim 6, in which said perfusion tube is constructed of material which is sufficiently flexible to enable insertion of said device through a longitudinal incision in a blood vessel wall.

10. The device of claim 6, wherein said device includes a tubular stem attached to said perfusion tube, and wherein said valve includes a stopper mounted on a stopper handle, said stopper and said stopper handle being movable within said tubular stem by moving said stopper handle in a reciprocating manner relative to said tubular stem, whereby said stopper may be moved between a first position in which flow through said lumen is blocked, and a second position in which said lumen is open.

11. The device of claim 10, in which said stopper handle includes a tab for gripping said stopper handle.

12. A method of creating a bloodless surgical field in a portion of a blood vessel, while also enabling perfusion of blood through the surgical field during attachment of a bypass, said method comprising:

providing a perfusion tube having a first end and a second end, with an occlusive member disposed at each of said first and second ends, and a valve for controlling the flow of blood through said perfusion tube;

forming an incision in the blood vessel;

inserting said first end of said perfusion tube through the incision and into the vessel, said occlusive member on said first end forming a sealing engagement with the inner wall of the vessel to stop the blood flow through the vessel, and said valve being in a position to prevent blood flow through said perfusion tube;

inserting said second end of said perfusion tube into said vessel through said incision by flexing said perfusion tube, said occlusive member on said second end forming a sealing engagement with the inner wall of said vessel; and adjusting said valve for allowing blood to flow through said lumen of said perfusion tube during attachment of the bypass.

13. The method of claim 12, further including a tubular stem connected to said perfusion tube for facilitating handling thereof.

14. The method of claim 13, wherein said valve includes a stopper mounted on a stopper handle, said stopper and said stopper handle being movable within said tubular stem by moving said stopper handle in a reciprocating manner relative to said tubular stem, whereby said stopper may be moved between a first position in which flow through said lumen is blocked, and a second position in which said lumen is open.

15. The method of claim 14, further including the step of suturing a tubular bypass graft to the vessel at the incision prior to withdrawal of said perfusion tube through the incision.

16. The method of claim 14, further including the step of adjusting said valve to stop blood flow through said perfusion tube and withdrawing said device back through the incision.

17. The device of claim 12, wherein said occlusive members are shaped as truncated cones.

* * * * *